United States Patent
Memarzadeh

(10) Patent No.: US 9,732,108 B2
(45) Date of Patent: *Aug. 15, 2017

(54) HALOGENATED DI- AND TRISACCHARIDES, PHARMACEUTICAL FORMULATIONS, DIAGNOSTIC KITS AND METHODS OF TREATMENT

(71) Applicant: COMMON PHARMA, INC., San Carlos, CA (US)

(72) Inventor: Bahram Memarzadeh, San Carlos, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/071,080

(22) Filed: Nov. 4, 2013

(65) Prior Publication Data

US 2014/0065062 A1   Mar. 6, 2014

Related U.S. Application Data

(63) Continuation of application No. 12/310,988, filed as application No. PCT/US2007/020071 on Sep. 14, 2007, now Pat. No. 8,575,333.

(60) Provisional application No. 60/844,913, filed on Sep. 14, 2006.

(51) Int. Cl.
*A61K 31/715* (2006.01)
*C07H 3/04* (2006.01)
*C07H 3/06* (2006.01)
*C07H 5/02* (2006.01)

(52) U.S. Cl.
CPC ............. *C07H 3/04* (2013.01); *A61K 31/715* (2013.01); *C07H 3/06* (2013.01)

(58) Field of Classification Search
CPC ................................................... A61K 31/715
USPC .... 536/123, 123.1, 123.13, 124; 514/53, 54, 514/61
See application file for complete search history.

(56) References Cited

U.S. PATENT DOCUMENTS

| | | | | |
|---|---|---|---|---|
| 5,498,709 A | * | 3/1996 | Navia | C07H 5/02 127/46.3 |
| 7,029,717 B1 | * | 4/2006 | Ojima et al. | 426/548 |
| 8,575,333 B2 | * | 11/2013 | Memarzadeh | A61K 31/715 536/123 |

* cited by examiner

*Primary Examiner* — Sudhakar Katakam
*Assistant Examiner* — Everett White
(74) *Attorney, Agent, or Firm* — Owen J. Bates

(57) ABSTRACT

The present invention relates to a novel family of alkylated halogenated di- and trisaccharides which exhibit pharmaceutical efficacy in the areas of permeation enhancers, anti-microbial effects, anti-fugal effects, facilitation of diagnostic procedures. The invention further includes methods of treatment and diagnostic kits.

13 Claims, 1 Drawing Sheet

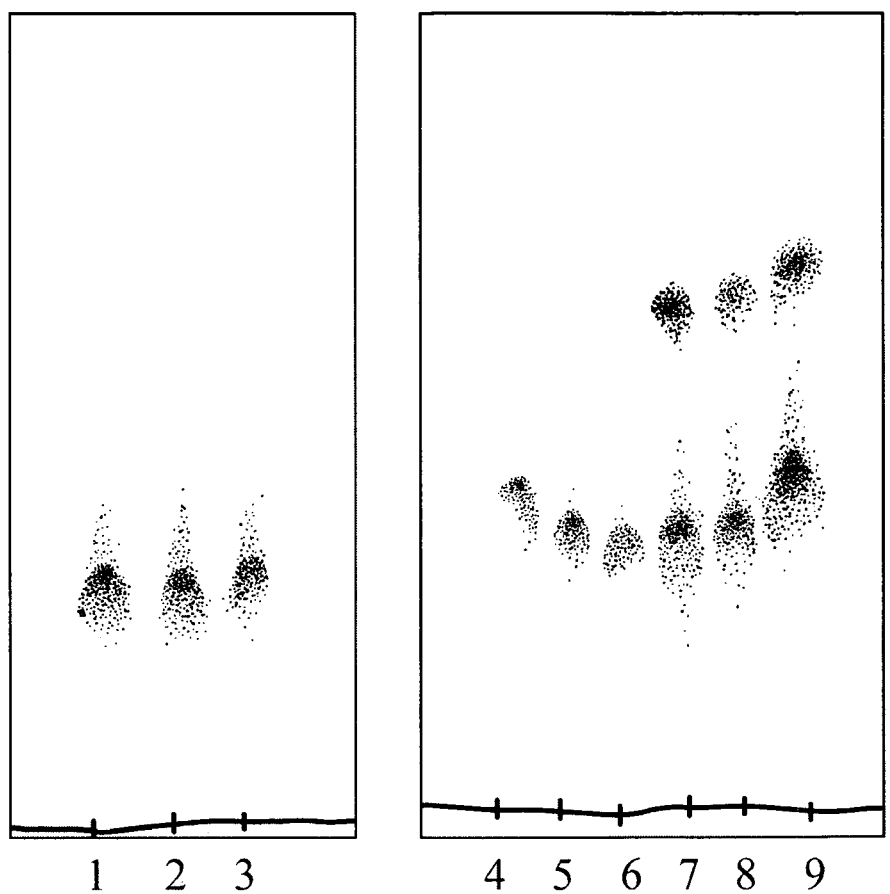

HALOGENATED DI- AND TRISACCHARIDES, PHARMACEUTICAL FORMULATIONS, DIAGNOSTIC KITS AND METHODS OF TREATMENT

CROSS REFERENCE TO RELATED APPLICATIONS

This application claims benefit of provisional application 60/884,913, filed 14 Sep. 2006, the entire contents of which are hereby incorporated by reference as if fully set forth herein, under 35 U.S.C. §119(e).

FIELD OF THE INVENTION

The invention relates to halogenated alkylated disaccharides and halogenated alkylated triscchararides used as biological membrane permeation enhancers, antimicrobial agents and surfactants, and anti-cancer agents.

Compounds

The compounds of the present invention are based upon disaccharides and trisaccharides, preferably disaccharides composed of hexoses and pentoses, and most preferably the following disaccharides:

1. Sucrose

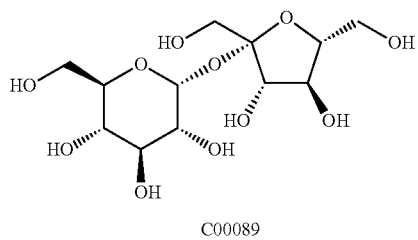

C00089

2. Lactose

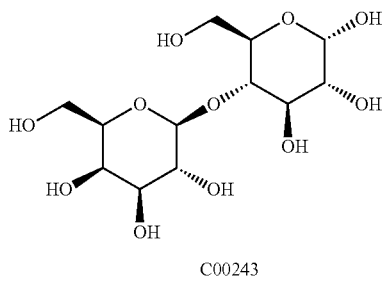

C00243

3. Maltose

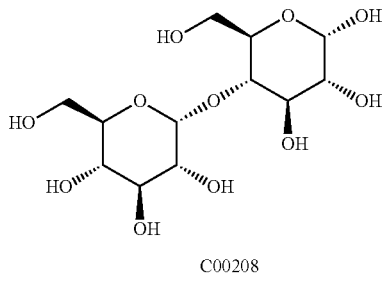

C00208

4. Isomaltose

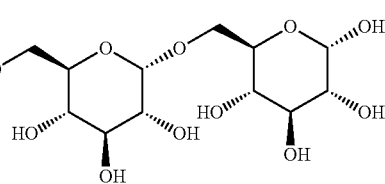

C00252

5. Trehalose

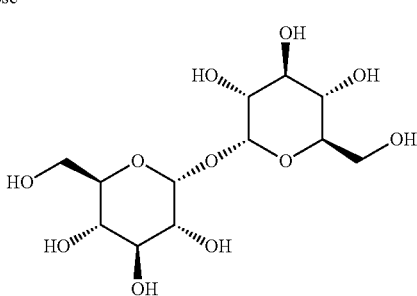

C01083

Representative compounds of the present invention encompass disaccharides and trisaccharides and more preferably the five structures shown above with the following substitutions:

One or more of the —OH groups attached directly to a ring carbon (secondary hydroxyls) being replaced by a halogen atom; and one or more of the —OH groups which are directly attached to a methylene group which is directly attached to a ring carbon (primary hydroxyls) being replaced by a halogen atom, an —O-ALK, or an —O—CO-ALK where ALK is any alkyl group.

Preferably one or more of the substituted halogens would be a chlorine atom and most preferably all of the substituted halogens would be chlorine. Specific compounds of the present invention include sucralose monolaurate, and a tri-chlorinated dodecyl maltose. Sucralose is the common name for 1',6'-dichloro-1,6'-dideoxy-β-D-fructofuranosyl-4-chloro-4-deoxy-α-D-galactopyranoside. Sucralose is sold as Splenda® by Johnson & Johnson.

Methods of Use.

The compounds of the present invention can be utilized as a biological membrane permeation enhancers, anti-fungal agents, anti-cancer agents, and anti-microbial agents as described below.

Permeation Enhancers

It has been well established that trans-membrane delivery of various therapeutic agents can be enhanced by sequential or simultaneous application of a permeation enhancer in conjunction with a therapeutic agent. Typical membranes that have been used for therapeutic agent delivery are dermal, mucosal and epithelial. Mucosal membranes include but are limited to gastrointestinal, sublingual, nasal, pulmonary, vaginal, oral, bladder, corneal and ocular membranes.

Dosage forms for applying and/or delivery the permeation enhancer and/or therapeutic agent include lozenges, tablets, capsules, suppositories, ointments, gels, biodegradable gels, bioerodible gels, osmotic pumps, active and passive patches, in both immediate and time release configurations. Such dosage forms could include various pharmaceutically acceptable buffers, stabilizers, adjuvants, fillers, binders and other components.

Mucosal tissue is a preferred site of enhanced therapeutic agent delivery with oral and bladder tissues being the most preferred.

Several examples of the method of enhanced therapeutic agent delivery through oral tissue are described below.

1. Two-Step Oral Rinse

In this first method, a first oral rinse is prepared having a therapeutically effective concentration of one of the permeation enhancing compounds of the present invention. The concentration will be effective to enhance the permeation of the active agent into and across the biological membranes of the oral cavity, as discussed below. This first oral rinse is introduced into the oral cavity and allowed to make contact with as much of the tissues of the oral cavity as possible. This can be accomplished by swirling, swishing and/or gargling the oral rinse. Then the rinse is expelled from the oral cavity. As an alternative, the first oral rinse can be swallowed if it is shown to be safe to do so.

Then a second oral rinse of an active agent is introduced into the oral cavity and allowed to make as much contact as possible with the biological membranes of the oral cavity. This can be accomplished by swirling, swishing and/or gargling the second oral rinse. As an alternative, the second oral rinse can be swallowed if it is shown to be safe to do so.

This method may require that each rinse needs to be repeated one or more times, with certain a waiting period needed between each rinse and a waiting period between treatments with the first and the second oral rinse.

By exposure of the tissues of the oral cavity to compounds of the present invention, the therapeutic efficacy of the active agent should be enhanced.

2. Two-Step Gel Formulations

A variation of the two-step method above would be to formulate the first oral rinse as a passive, bio-erodible and/or bio-degradable gel for application to the biological membranes of the oral cavity. The physical form of the gel helps to maintain it in contact with the surfaces of the biological membranes of the oral cavity so that the permeation enhancer compound of the present invention is in direct contact with the oral cavity which will increase its permeation enhancing efficiency. The gel is allowed to remain in the oral cavity for a predetermined period of time and then removed or allowed to remain until the gel has fully eroded or degraded.

The second oral rinse can also be formulated as a gel and used in the same manner as described above for the first oral rinse.

3. Combined Oral Rinse

Yet another variation would be to combine both a permeation enhancer compound of the present invention with a therapeutically active agent into a single oral rinse. In a manner similar to that described above, a therapeutically effective concentration of the permeation enhancer and a therapeutic agent would be formulated into single oral rinse and then introduced into the oral cavity.

4. Combined Gel Formulation

A variation of the combined oral rinse described in paragraph 3 above, would be to formulate the combined oral rinse as a passive, bio-erodible and/or bio-degradable gel for application to the biological membranes of the oral cavity. The physical form of the gel helps to maintain it in contact with the surfaces of the biological membranes of the oral cavity so the permeation enhancer compound of the present invention is in direct contact with the oral cavity which will increase its permeation enhancing efficiency. The combined gel is allowed to remain in the oral cavity for a predetermined period of time and then removed or allowed to remain until the gel has fully eroded or degraded. Because both the permeation enhancer and the therapeutic agent are incorporated into the single combined gel formulation, only one application of the combined gel is necessary to effectuate delivery of the therapeutic agent.

Is should be noted that all formulations may include secondary agents in addition to the permeation enhancer and the active agent. Such secondary agents might included but are not limited to formulation anti-microbials, topical anti-microbials, anti-fungals, local anesthetics, analgesics, pain-relievers, and anti-pyretics, and buffers.

Indications

This methods described above are for the topical treatment of diseases localized in the oral cavity and related tissues, including but not limited to lips, teeth, gums, pharynx, tongue, and other tissues that are in sufficient proximity these tissues that they can be treated with the formulations of the present invention.

Such diseases include but are not limited to oral mucositis and oral cancer. Oral mucositis is a debilitating complication of oral cancer therapy. It results in the inflammation of the mucosa of the oral cavity which can range from simple redness and irritation to severe ulcerations. It can sometimes be so severe that the patient cannot tolerate food or fluids and the cancer therapy is discontinued. The severe ulcerations and the weakened immune systems often result in opportunistic infections which complicates both the treatment of the oral mucositis and the cancer.

Procedures and methods similar to the above oral procedures can be adapted for use in the delivery of chemotherapeutic agents through the bladder mucosa.

Gene Therapy/Oncolytic Viral Vectors

Viruses play an important role in modem therapeutic treatments. Viruses can be used to introduce genetic material into cells in order to treat indications caused my missing or malfunctioning genes. In addition, several classes of viruses are known to be effective in destroying cancer cells.

It has been shown that dodecyl maltoside and sucrose monolaurate have been effective in increasing the effectiveness of gene and oncolytic virus therapy. (*Identification of Pretreatment Agents to Enhance Adenovirus Infection of Bladder Epithelium*, Ramesh et al., Molecular Therapy, 2004, October; 10 (4):697-705).

As discussed previously, it is anticipated that the addition of halogen atoms to alkyl disaccharides, yielding the chlorinated alkyl disaccharides of the present invention, would increase the permeation enhancing qualities of these compounds.

Diagnostic Uses

In addition, the above method can be used to enhance the efficiency of diagnostic oral staining reagents, such as toluidine blue, as well as enhance the efficiency of radioactive-labeled diagnostic reagents. See "Toluidine Blue Staining Identifies High-Risk Primary Oral Premalignant Lesions with Poor Outcome", Zhang et al., Cancer Research 2005, 65: (17), Sep. 1, 2005.

To facilitate diagnostic use of the halogenated alkyl disaccharides, the present invention includes kits, preferably diagnostic kits, which would include one or more of the following components:

the permeation enhancer prepackaged in a container that allows for easy dispensing of a predetermined aliquot or one or more pre-measured aliquots in single use packaging;

other agents needed to perform the diagnostic method which would typically include but not be limited to staining agents and/or radioactive diagnostic agents.

Similarly, these other agents could be packaged in containers that allows for easy dispensing of a predetermined aliquot or one or more pre-measured aliquots in single use packaging;

detailed written instruction regarding the proper method of performing the diagnostic procedure; and packaging which would hold all of the components to the kit.

Anti-Microbial Activity

It has been shown that sucrose monolaurate has can be an effective anti-microbial against *Listeria Monocytogenes* when used in conjunction with certain organic acids. "Inhibitory effects of sucrose monolaurate, alone and in combination with organic acids, on *Listeria Monocytogenes* and *Staphylococcus aureus*, J. Applied Bacteriol. 1996; 81 (1):7-18.

It is anticipated that this same effect will be enhanced for sucralose monolaurate, other alkylated sucraloses, as well as other halogenated alkylated disaccharides.

Anti Microbial Testing

The preferred embodiment was tested for antimicrobial activity using the following procedure.

A 1% solution of Compound 3 was prepared in DPBS (Dulbecco's phosphate buffered saline). A 25 ml mixture of the 1% Compound 3 and PBS (phosphate buffered saline, pH 7.2 was prepared by mixing 5 ml of the 1% Compound 3 solution and 20 ml of the PBS.

A 10 ml aliquot of the above mixture was placed into each of two sterile test tubes. One test tube was inoculated with 0.1 ml of *S. aureus* and the other with 0.1 ml of *P. aeruginosa*, such that there was a final concentration of $10^6$ colony-forming units (CFU)/0.1 mls.

A various time points, 1.0 ml of each inoculated test sample were removed, diluted 10× with 0.45% saline and plated on trypticase soy agar (TSA) plates.

Samples of PBS was treated in the same manner. At time points 5 mins and 60 mins, two 1 ml samples were taken and diluted 10× and one spiked with a 0.1 ml aliquot of the *S. aureus* and the other spiked with 0.1 ml of the *P aeruginosa*. These samples were the PBS challenge and the data is shown below.

The plates were incubated at 30-35° C. for not less than 24 hours. Concentration of CFU in the samples taken at each time point were enumerated by standard methods. The log reduction was calculated for each time period and organism. The log reduction was calculated using the formula: Log reduction=Log inoculums verification−sample log recovery.

The material was considered antimicrobial if it showed a greater than 5 log reduction of each challenge organism compared to the theoretical inoculum of the same organism.

These data show that Compound 3 has antimicrobial effect against *S. aureus* but not *P. aeruginosa*

Test Results

| | Compound 3 | | |
|---|---|---|---|
| Organism | Time (minutes) | Concentration (CFU/mL) | Log Reduction |
| *Staphylococcus aureus* | 5 | $6.9 \times 10^5$ | 4 |
| | 15 | $4.3 \times 10^4$ | 5.2 |
| | 30 | $1.41 \times 10^4$ | 5.7 |
| | 60 | $2.9 \times 10^3$ | 6.3 |

-continued

| Organism | Time (minutes) | Concentration (CFU/mL) | Log Reduction |
|---|---|---|---|
| *Pseudomonas aeruginosa* | 5 | $1.53 \times 10^6$ | 3.5 |
| | 15 | $1.1 \times 10^6$ | 3.7 |
| | 30 | $1.21 \times 10^6$ | 3.6 |
| | 60 | TNTC* | TNTC* |

| | PBS Challenge | | |
|---|---|---|---|
| Organism | Time (minutes) | Concentration (CFU/mL) | Log Reduction |
| *Staphylococcus aureus* | 5 | TNTC | TNTC** |
| | 60 | $8.4 \times 10^6$ | 2.9 |
| *Pseudomonas aeruginosa* | 5 | $2.46 \times 10^6$ | 3.3 |
| | 60 | $1.87 \times 10^6$ | 3.4 |

| | Inoculum Verification | |
|---|---|---|
| Organism | Concentration (CFU/mL) | Log |
| *Staphylococcus aureus* | $6.0 \times 10^9$ | 9.8 |
| *Pseudomonas aeruginosa* | $5.0 \times 10^9$ | 9.7 |

*TNTC = too numerous to count or not consistent. Log reduction not able to be calculated
**To Numerous to count for all dilutions. Log reduction could not be calculated.

Surfactants

A described in the report "The Potential Sucrose Esters in Detergent Compositions" by Mary An Godshall of the Sugar Processing Research Institute, Inc., sucrose esters are non-ionic surfactants. Ionic surfactants can form complexes with various other ions which can be problematic and adversely effect performance. Thus non-ionic surfactants are preferred.

Sucrose esters have been approved by the FDA for use in various topical applications such as cosmetics and shampoos as well as consumed items as such as soft drinks and salad dressings.

It is anticipated that halogenated sucrose esters, as well as other halogenated alkyl disaccharides will function at least as effectively as the sucrose esters. By varying the size of the alkyl groups, solubility and melting point can be altered.

Method of Synthesis—Synthesis 1

Compounds of this invention can likely be synthesized by the method described in "Chemical versus enzymatic catalysis for the regioselective synthesis of sucrose esters of fatty acids", Ferrer et al., *Studies in Surface Science and Catalysis*, 130, 509-514 (2000) Elsevier. As described, a lauryl group is added to the 2-OH and 3-OH group of sucrose by reacting vinyl laurate with sucrose in a reaction mixture of $Na_2HPO_4$, Celite, and Eupegit C using DMSO as a solvent at 40° C. It is anticipated that this same type of reaction would be successful using the various halogenated disaccharides as a starting material to produce the alkylated chlorinated disaccharides of the present invention. The addition of the halogen atoms to the disaccharides is not anticipated to significantly alter the reactivity of the —OH groups.

Replacement by a halogen of various —OH groups on aromatic rings is a well established reaction technique and the halogenated disaccharides would be used as the starting material in the alkylation reaction described above.

In addition to the alkylating reaction provided above, two other alkylation reactions are provided below. Though each is shown using a different reaction procedure which resulted in a different alkyl moiety, it is expected that each of the techniques provide below can be used to modify various halogenated disaccharides with various alkyl groups.

Detailed procedures for two specific synthesis methods for making halogenated alkylated disaccharides are provide below.

Synthesis of Sucralose Monomyristate

1',6'-Dichloro-1',6'-dideoxy-β-D-fructofuranosyl-4-chloro-4-deoxy-6-O-monotetradecanoate-α-D-galactopyranoside.

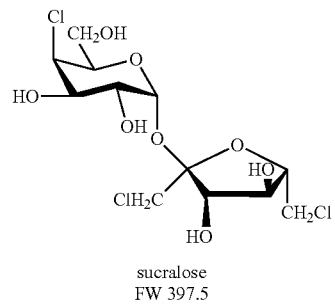

sucralose
FW 397.5

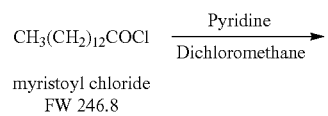

myristoyl chloride
FW 246.8

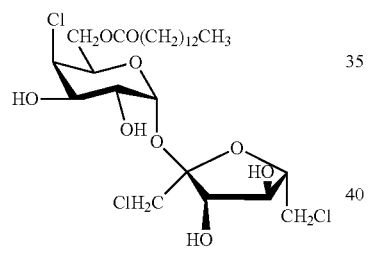

sucralose monomyristate
FW 607.52

| Raw Materials | FW | Quantity used (mmol) |
| --- | --- | --- |
| sucralose | 397.5 | 3 g (7.54 mmol) |
| myristoyl chloride | 246.8 | 1.5 mL (1.2 molar eq.) |
| pyridine | 79.1 | 3 mL |
| dichloromethane | 84.93 | 5 mL |

The Process:

To Sucralose (3 g, 7.54 mmol) in 3 mL pyridine and 5 mL dichloromethane at −25° C., myristoyl chloride (1.5 mL, 1.2 molar eq.) was added dropwise. The solution was allowed to warm to room temperature over a period of 1.5 h. Thin layer chromatography (3% methanol in chloroform) showed a new spot (product) and traces of the starting material remaining. Methanol was added to remove excess myristoyl chloride, and the mixture was evaporated to dryness under reduced pressure. The residue is chromatographed on a column of silica gel eluting with same solvent (3% methanol in chloroform), to give in the average of 70% yield of the sucralose monomyristate as a white amorphous solid.

Synthesis of Sucralose Monolaurate

1',6'-Dichloro-1',6'-dideoxy-β-D-fructofuranosyl-4-chloro-4-deoxy-6-O-monododecanoate-α-D-galactopyranoside.

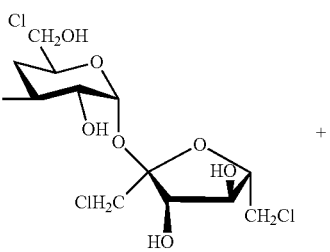

sucralose
FW 397.5

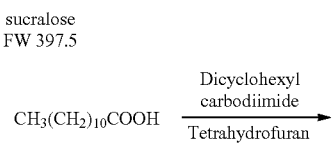

lauric acid
FW 200.3

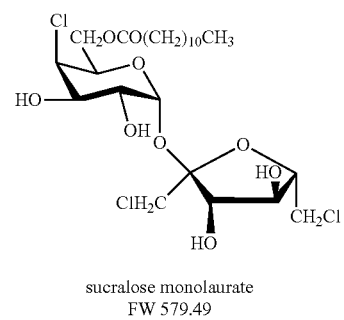

sucralose monolaurate
FW 579.49

| Raw Materials | FW | Quantity used (mmol) |
| --- | --- | --- |
| sucralose | 397.5 | 2 g (5.03 mmol) |
| lauric acid | 200.3 | 1 g (4.99 mmol) |
| dicyclohexyl carbodiimide | 206.3 | 1 g (4.84 mmol) |
| tetrahydrofuran | 72.1 | 5 ml |

The Process:

Lauric acid (1 g, 4.99 mmol) in 2 mL tetrahydrofuran was stirred with dicyclohexyl carbodiimide (1 g, 4.84 mmol) at room temperature for 5 minutes. Sucralose (2 g, 5.03 mmol) in 3 mL tetrahydrofuran was added and the mixture stirred overnight at room temperature. Thin layer chromatography (3% methanol in chloroform) showed a new spot (product) and traces of the starting material remaining. The mixture was evaporated and the residue chromatographed on a column of silica gel eluting with same solvent (3% methanol in chloroform), to give in the average of 60% yield of the sucralose monolaurate as a white amorphous solid.

Method of Synthesis-Synthesis 2
Preparation of Sucralose Monolaurate (3)

[Structure of Sucralose (1)]

[Structure of Lauroyl chloride (2): O=C(Cl)(CH₂)₁₀CH₃]

→ 2 →

[Structure of Sucralose Monolaurate (3)]

| Compound | Formula Weight | Amount | Mmoles |
|---|---|---|---|
| Sucralose (1) | 379.5 | 10.01 grams | 25.2 mmoles |
| Lauroyl chloride (2) | 218.77 (d = 0.922) | 5.6 mL | 25.2 mmoles |
| Pyridine | | 10 mL | |
| Tetrahydrofuran | | 100 mL | |

1. Sucralose (1) (10.01 g, 25.2 mmoles) was dissolved in anhydrous tetrahydrofuran (100 mL) and pyridine (10 mL) was added. The mixture was cooled to −25 deg C. under nitrogen.
2. Lauroyl chloride (2) (5.6 mL, 25.2 mmoles) was added dropwise over 20 minutes. After addition of the lauroyl chloride, the reaction mixture was allowed to warm from −25 deg C. to room temperature over 1.5 hours.
3. The resulting mixture was diluted with ethyl acetate (300 mL) and organics were washed sequentially with:
   a. water (2×50 mL),
   b. 1M HCl (in water, 3×50 mL),
   c. sodium bicarbonate (saturated aqueous, 3×50 mL),
   d. water (2×50 mL),
   e. copper sulfate (saturated aqueous, 3×25 mL) and
   f. sodium chloride (saturated aqueous, 2×50 mL).
4. TLC plates were spotted with the washed organic phase and then chromatographed with 10% methanol in methylene chloride). The plates were dried and then sprayed with a 5% phosphomolybidic acid solution and then heated until spots were visible. The TLC analysis the washed organic phase revealed the presence of a major spot (Rf=0.3) accompanied by minor amounts of starting material and byproducts.
5. The washed organic phase was dried over anhydrous sodium sulfate, filtered and concentrated to dryness. The residue was purified on by flash chromatography on silica gel. The column was eluted with 8% methanol in methylene chloride which yielded three sets of fractions (lanes 1-3, FIG. 1).
6. Fraction set 1 (1.6 grams) contained mostly pure material as determined by TLC analysis (10% methanol in methylene chloride). Fraction sets 2 and 3 contained significant impurities and require further purification. A complete TLC analysis is shown in FIG. 1.

Material from Synthesis 1 was co-eluted with material from Fraction set 1 (Lane 7, FIG. 1).

Using 10.01 grams of sucralose, the theoretical isolated yield of compound 3 was 15.3 grams. While the isolated material from Fraction Set 1 (1.6 grams) represents only a 10.5% yield, purification of Fraction sets 2 and 3 would be expected to yield significantly more material.

FIG. 1. TLC analysis (10% methanol in methylene chloride) of the conversion of compound 1 to compound 3.
Lane 1 is Fraction Set 1 (hightest purity) from silica gel chromatography.
Lane 2 is Fraction Set 2 (intermediate purity) from silica gel chromatography.
Lane 3 is Fraction Set 3 (very low purity) from silica gel chromatography.
Lane 4 is crude product from the washed organic phase of the reaction mixture.
Lane 5 was co-spotted with crude material from the washed organic phase of the reaction mixture and Fraction Set 1 from silica gel chromatography.
Lane 6 is Fraction Set 1 from silica gel chromatography.
Lane 7 was co-spotted with Fraction set 1 from silica gel chromatography and a sample of the reaction mixture from Synthesis 1.
Lane 8 is a sample of compound 3 obtained by Synthesis 1
Lane 9 was a co-spotted with crude material isolated from the reaction mixture, Fraction Set 1 from silica gel chromatography of Synthesis 2 and a sample of the reaction mixture obtained via Synthesis 1.

HPLC/Mass Analysis of Fraction Set 1 (Lane 1, FIG. 1)

A solution of Fraction Set 1-Synthesis 2 (the purest fraction set) was prepared at a concentration of 10 mg/mL in DMSO. To prepare for LC-MS analysis the solution was diluted to 0.1 mg/mL in 5% methanol containing 0.2% formic acid. Samples were analyzed using the following LC/MS/MS conditions:
HPLC: Shimadzu VP System
Mobile Phase: A-0.2% formic acid in water
B-0.18% formic acid in methanol
Column: 1×50 mm BetaBasic C18
Injection Volume: 5 μl
Gradient: 5-95% B in 5 minutes
Flow Rate: 100 μl/min
Mass Spectrometer: Applied Biosystems/MDS SCIEX Q-STAR
Interface: IonSpray split at ~1/10
Parent Ion Scan: TOF Negative from 300-1200 amu There was a single peak that eluted from the reverse phase column at 6.66 minutes. Mass detection of the components of that peak showed 5 components having masses of:

| Mass | Intensity Counts |
|---|---|
| 577.1655 | 38 |
| 578.1696 | 13 |
| 579.1622 | 40 |
| 579.2698 | 14 |
| 581.1613 | 15 |

These mass determinations are consistent with the theoretical molecular weight of sucralose monolaurate, taking into account the variations in mass due to the existence of the $^{35}Cl$ and $^{37}Cl$ isotopes of chlorine and minor random fragmentation.

To those skilled in the art it will be understood that there can be many other variations of the embodiments what have been described above while still achieving the same objectives of the invention. Such variations are intended to be covered by the scope of this invention. As such, the foregoing description of embodiments of the invention is not intended to be limiting. Accordingly, it is intended that the appended claims will cover all modifications of the invention that fall within the true spirit and scope of the invention.

What is claimed is:

1. A compound comprising an oligosaccharide selected from the group consisting of a disaccharide and a trisaccharide wherein one or more of the secondary hydroxyls of said oligosaccharide are substituted with a halogen atom, wherein one or more of the primary hydroxyls of said oligosaccharide are substituted by an —O-ALK or an —O—CO-ALK, wherein one or more of the primary hydroxyls are substituted by a halogen atom, and wherein said ALK group is comprised of 6 to 14 carbons.

2. A compound as described in claim 1 comprising a disaccharide wherein one or more of the secondary hydroxyls of said disaccharide are substituted with a halogen atom, wherein one or more of the primary hydroxyls of said disaccharide are substituted by an —O-ALK or an —O—CO-ALK and wherein one or more of the primary hydroxyls are substituted by a halogen atom.

3. A compound as described in claim 1 comprising a trisaccharide wherein one or more of the secondary hydroxyls of said trisaccharide are substituted with a halogen atom, wherein one or more of the primary hydroxyls of said trisaccharide are substituted by an —O-ALK or an —O—CO-ALK and wherein one or more of the primary hydroxyls are substituted by a halogen atom.

4. A compound as described in claim 1 wherein said oligosaccharide is comprised of monosaccharides selected from the group consisting of a hexose and a pentose.

5. A compound as described in claim 4 wherein said oligosaccharide is a disaccharide comprising one pyranose and one furanose.

6. A compound as described in claim 5 wherein said disaccharide is sucrose.

7. A compound as described in claim 6 wherein one secondary hydroxyl on the pyranose ring is substituted with a halogen atom, wherein each of two primary hydroxyls on the furanose ring are substituted by a halogen atom.

8. A compound as described in claim 7 wherein said halogen atom is a chlorine atom.

9. A compound as described in claim 4 wherein said oligosaccharide is a trisaccharide.

10. A pharmaceutical formulation comprising a compound as described in claim 1.

11. A pharmaceutical formulation as described in claim 10 wherein said formulation is contained in a dosage form selected from the group consisting of lozenges, tablets, capsules, ointments, gels, biodegradable gels, bioerodible gels, suppositories, active and passive transdermal patches, osmotic pumps and IV solutions in immediate or timed release configurations.

12. A kit for performing a diagnostic procedure comprising:
 a compound as described in claim 1 which is prepackaged in a container that allows for easy dispensing of a predetermined aliquot or one or more pre-measured aliquots in single use packaging;
 one or more additional ingredients needed to perform the diagnostic procedure, such additional ingredients packaged in containers that allow for easy dispensing of a predetermined aliquot or one or more pre-measured aliquots in single use packaging;
 detailed written instructions regarding the proper method of performing the diagnostic procedure; and
 packaging which would hold all of the components of the kit.

13. A kit as described in claim 12 wherein said additional ingredients would be selected from a group consisting of staining agents and radioactive diagnostic agents.

* * * * *